United States Patent [19]

Carels, Jr.

[11] Patent Number: 4,981,144

[45] Date of Patent: Jan. 1, 1991

[54] URINE SEPARATION AND COLLECTION DEVICE

[75] Inventor: Henry A. Carels, Jr., 50281 Bellaire Dr., New Baltimore, Mich. 48047

[73] Assignee: Henry A. Carels, Jr., New Baltimore, Mich.

[21] Appl. No.: 881,920

[22] Filed: Jul. 3, 1986

Related U.S. Application Data

[63] Continuation-in-part of Ser. No. 712,652, Mar. 18, 1985, abandoned.

[51] Int. Cl.⁵ .................. A61B 5/00; A61B 10/00
[52] U.S. Cl. .................................. 128/760; 128/762; 141/237
[58] Field of Search ................... 128/760–762, 128/767, 771; 222/460–462; 141/236–237, 242, 244, 297, 331, 334

[56] References Cited

U.S. PATENT DOCUMENTS

| | | |
|---|---|---|
| D. 205,236 | 7/1966 | Ilg ........................................ 141/331 |
| 2,791,494 | 5/1957 | Thompson . |
| 3,196,909 | 7/1965 | Monk .................... 141/237 |
| 3,202,167 | 8/1965 | De Young et al. . |
| 3,381,862 | 5/1968 | Selzler ................... 222/460 |
| 3,405,706 | 10/1968 | Cinqualbre . |
| 3,494,351 | 2/1970 | Horn .................... 128/762 |
| 3,604,410 | 9/1971 | Whitacre ................ 128/762 |
| 3,695,486 | 10/1972 | Warner ................ 141/242 X |
| 3,781,922 | 1/1974 | Ericson . |
| 3,859,671 | 1/1975 | Tomanello ............ 128/762 X |
| 3,894,845 | 7/1978 | McDonald . |
| 3,894,854 | 7/1975 | Wells . |
| 3,922,913 | 12/1975 | Scott ................ 128/762 X |
| 3,982,898 | 9/1976 | McDonald ............ 128/762 X |
| 4,042,337 | 8/1977 | Griffith ................ 128/762 X |
| 4,140,178 | 2/1979 | Olshwager et al. . |
| 4,206,767 | 6/1980 | Wingrove ............... 128/762 |
| 4,265,065 | 5/1981 | Osada .................. 222/460 X |
| 4,296,748 | 10/1981 | Kurtz et al. ............ 128/762 X |
| 4,335,730 | 6/1982 | Griffin .................. 128/760 |
| 4,345,342 | 8/1982 | Saito .................. 128/762 X |
| 4,461,328 | 7/1984 | Kenney . |
| 4,492,258 | 1/1985 | Lichtenstein ........... 141/331 X |
| 4,554,687 | 11/1985 | Carter et al. .......... 128/760 X |
| 4,569,090 | 2/1986 | Muller ................ 128/762 X |
| 4,888,922 | 6/1983 | Telang ................... 604/319 |

FOREIGN PATENT DOCUMENTS 1208412 10/1970 United Kingdom ........... 128/762

Primary Examiner—Ruth S. Smith
Assistant Examiner—John P. Lacyk
Attorney, Agent, or Firm—Brooks & Kushman

[57] ABSTRACT

Urine or other liquid is automatically divided into equal amounts upon being poured into the inlet opening of a manifold having a tubular body and its upper end and a plurality of outlets adjacent its lower end. Substantially equal amounts of fluid exit each outlet and are received by a plurality of independent fluid chambers.

18 Claims, 2 Drawing Sheets

URINE SEPARATION AND COLLECTION DEVICE

RELATED APPLICATIONS

This application in a continuation-in-part of Ser. No. 712,652 filed Mar. 18, 1985, now abandoned.

DESCRIPTION

1. Field of Invention

This invention relates to the field of urine sample collecting devices and more particularly to urine collecting devices which automatically divide the sample into several parts.

2. Background of Invention

Urinary tests are an important diagnostic tool utilized by the medical profession. A whole variety of different tests may be run on urine samples which provide a simple non-intrusive method of obtaining valuable data relating to the patient's metabolism. Since urinary samples of a given patient may vary from discharge to discharge during the day, it is a common practice to collect a timed sample, typically a 24-hour specimen. A 24-hour specimen is obtained by accumulating the total urinary output of the patient during the test interval. The total volume can be measured and the comingled sample can be tested at the end of the period. When more then one chemical analysis is to be conducted in the laboratory, small portions of the 24-hour specimen are withdrawn and used for the various tests.

Urine samples, unfortunately, will tend to degrade with time especially at room temperature and significant degradation will occur within a 24-hour period detrimentally affecting the quality of the test results. To minimize such spoilage of the sample, it is common to use a variety of chemical preservatives which are placed in the collection vessel. It is important to use a preservative which will not detrimentally affect the chemical analysis to be subsequently conducted. There is no one all-purpose preservative that will be suitable for all tests. Therefore, when it is desired to conduct multiple tests which require incompatible preservatives, it is necessary to use preservatives and refrigerate the collection vessel or have multiple collection vessels and divide each discharge equally between the various collection vessels containing different preservatives. A mechanism designed for such a purpose is the urine collection device of Griffin shown in U.S. Pat. No. 4,042,337. Other urine collection devices are shown in U.S. Pat. Nos. 3,922,913 and 4,206,767.

The following list identifies the most frequently run urinary chemistry tests:

Albumin
Aldosterone
Amino Acids
Amylase
Barbiturates
Bence Jones Protein
Calcium
Catecholamines
Chlorides
Chlorionic Godanotropins
Creatine
Creatinine
Creatinine Clearance
Epinephrine, Norepinephrine, Metanaphrine
Estrogens
Estriol
Glucose
Hydroxyproline
Immuno Gloubins
Iron
Ketones
Ketosteroids
Lactic Dehydrogenase
Lead
Lipase
Magnesium
Nitrogen Total
Osmolality
Oxalate
Phosphorus
Pituitary Gonadotropins
Porphobilinogen
Porphyrins
Potassium
Pregnandiol
Pregnanetriol
Protein
Serotonin
Sodium
Urea Nitrogen
Uric Acid
Urobilinogen
Uroporphyrins
VMA
Zinc One or more of the following preservatives or storage procedures will adequately preserve a 24-hour urine sample for use in the previously-listed chemical tests:

Sodium Fluoride
Sodium Benzolate
Boric Acid
Toluene
Hydrochloric Acid
Sodium Hydroxide
Nitric Acid
Glacial Acetic Acid
Ice Bath or Refrigeration
Protection from Light One of the principal objects of the present invention is to enable a timed urine sample to be collected automatically and accurately divided into a number of equal portions.

Another object of the invention is to provide a device and method for collecting urine in a number of independent containers with the absolute minimum amount of handling and spillage during collection as well as the subsequent removal of samples.

A purpose of this device is to allow the urinary output of various chemicals to be calculated simultaneously by multiplying the measured concentration of the chemical in a specific chamber and the total volume collected in all chambers for a given period of time.

A further object of the invention is to develop a urine collection device which automatically divides a sample into equal portions which is not affected by small variations in collection device levelness or the manner in which the urine is poured into the device.

A significant advantage of the present invention is that urine can be accurately divided into a number of equal independently stored portions.

Another important advantage of the present invention is that the device may be opened and a urine sample withdrawn without spillage.

These and other objects in the future of the invention will be further understood upon review of the drawings and the following description.

SUMMARY OF INVENTION

I have developed an apparatus and method by which urine samples will be automatically divided into equal, independent portions. The apparatus comprises a generally vertical manifold having an upper input and a plurality of outputs at the lower end.

The lower end of the manifold in the region of the outlets is inwardly conically tapered. Each of the set outputs are connected with independent fluid storage reservoirs. The device is preferably provided with an enlarged funnel section communicating with the inlet end of the manifold.

This invention separates and collects sequential multiple urine specimens into a plurality of equally volumed compartments. The deposited specimens, collected over a period of time, constitute the urinary output for that given time period. The measurement of the urinary output of a particular chemical requires the concentration and total volume excreated during that time period. Since urinary concentration varies with each specimen voided, it is necessary to know the average concentration over a given period of time. This invention permits an equal volume of each deposited specimen to flow into each compartment unchanged, thereby constituting identical urinary chemistry compositions. Each compartment may have added prior to, simultaneous with, or after collection a variety of enhancers, buffers, stabilizers, or preservatives necessary to facilitate the most accurate and precise analysis.

The device consists of a collecting chamber and separation system, with the ability to divide a fluid into a plurality of equally volumed proportions, while allowing the so-divided volume to be chemically preserved, enhanced, stabilized or altered in a variety of ways for the purposes of preservation, reactivity, qualitative and quantitative analysis.

BRIEF DESCRIPTION OF THE PREFERRED EMBODIMENT

With reference to the drawings, the novel urine collection and separating device will be hereinafter described.

This invention allows urine to be divided into equal portions and collected in chambers containing various preservatives as each specimen is poured into the top of the container. It is necessary that a portion of each specimen collect in each chamber so that the composition will reflect the total urinary output during that time interval. The most common timed urinary collection is a 24-hour urine specimen, however, 4, 8, or 12-hour timed specimens are possible. The ability to separate urine into multiple containers in a representative manner permits the addition of a variety of preservatives, stabilizers, and reagents to be added to the separate compartment containers which facilitates the performance of a variety of tests on a single timed urine collection of measured volume. This is in contrast to the present method which requires a repetitive collection for each test if it requires a different additive.

Figure 1:
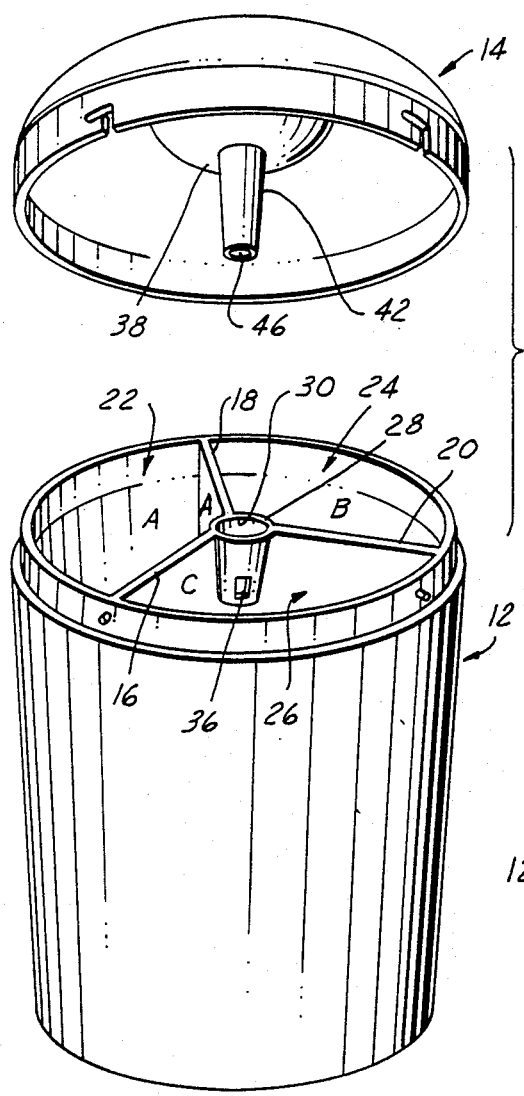
FIG. 1 is an exploded perspective view showing a preferred embodiment of the urine collecting and separating device.

FIG. 1 shows an exploded perspective view of the urine collecting device 10 which is two main components, a base 12 and a cover 14. The base is a pail-like container having three internal partitions 16, 18, and 20 which divide the base into three independent fluid-tight regions 22, 24, and 26, each of which is a generally pie-shaped segment of the cylindrical base member. A manifold member 28 is centrally located and the top portion of the base at the intersection of the three interior partitions 16, 18 and 20. The manifold extends vertically along the central axis of the base and is provided with an inlet opening 30 at its upper end. The sides of the manifold taper inwardly and at the lower end of the manifold are three outlet ports, 32, 34, and 36, each of which communicates with a fluid region 22, 24, and 26 respectively. The tubular body of the manifold is aligned along a generally verticle axis with the outlet port circumferentially spaced apart and radially projecting from the axis. When urine or other fluid is poured into the manifold inlet 30 the urine flows downwardly to the lower end of the manifold flowing out of the three outlet ports in substantially equal quantities.

This invention has the property to separate fluid of varying composition into an equal and plural number of volumes while maintaining the distinct composition of the liquids so deposited. This characteristic can be repeatedly utilized for multiple deposits yielding a timed collection of fluid in a plurality of compartments with identical compositions.

Figure 2:
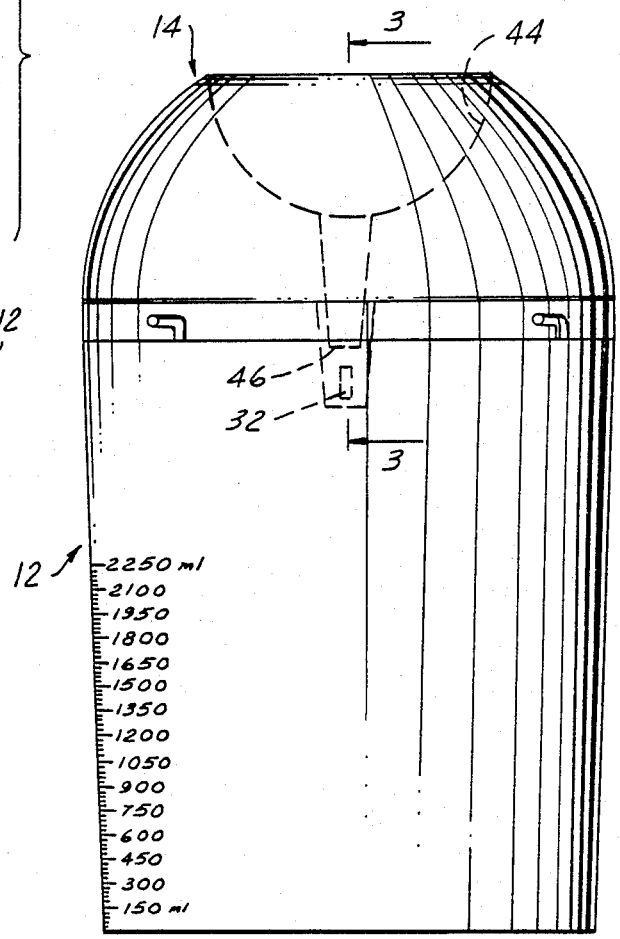
FIG. 2 is a side elevation of the assembled device shown in FIG. 1.
Figure 3:
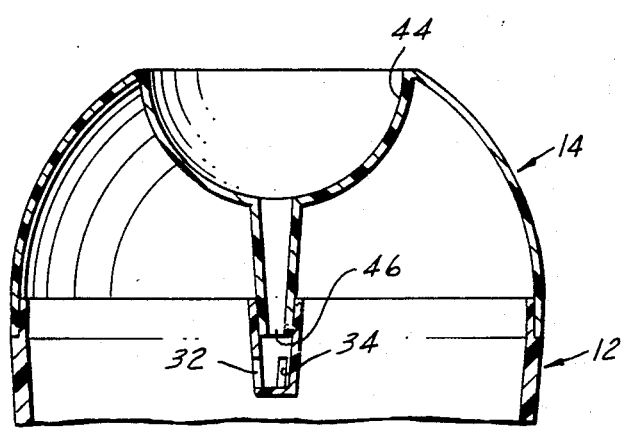
FIG. 3 is a partial cross-sectional view of the device taken along line 3—3 in FIG. 2.

The cover 14 portion of the urine collecting device 10 is provided with a funnel 38 formed therein. Funnel 38 has an enlarged mouth portion with an inlet 44 which is connected to a tapered neck portion 44. When the cover is installed on the base, as shown in FIG. 2, the neck 44 of the cover 42 fits securely within the inlet 30 of the manifold in the base. The funnel portion not only serves to ease the pouring of urine into the device but serves to accumulate urine during the dividing process and to carefully direct a uniform stream of urine axially into the manifold region thereby preventing the incoming flow to favor any one individual outlet port. The funnel has an enlarged opening 44 and the constricted outlet opening 46. The fact that the funnel outlet 46 is smaller in diameter than the adjacent portion of the manifold further aids in the even distribution of urine out each of the outlet ports. The exterior wall of the funnel neck which cooperates with the manifold ideally has matching conical surfaces so that a good fluid-tight seal may be established. Preferably outlets extend radially relative to the axis of the manifold an funnel assembly which further promotes even distribution. Note that the size of the outlet ports should be carefully controlled so that they are uniform and free from burrs and flash which would cause variation in the volume of fluid deposited in each of the fluid regions.

In use the entire urine collecting device may be placed in an ice bucket and chilled adjacent to the patient's bed. The compact structure of the present invention readily lends itself to chilling in an ice bucket. When the urine collecting device is placed in an ice bucket, it is frequently very difficult to keep it level. However, with the present invention, it is specifically designed so that minor variations in the levelness of the device will not significantly affect the volume distribution within the various fluid regions. After the end of the timed urine collection period, the entire urine collecting device can be conveniently shipped to the medical laboratory for analysis.

Typically, the lab personnel will remove the cover 14 from the base and extract from each of the fluid regions one or more samples to be used in chemical analysis. Each of the fluid reservoirs within the device is marked with some sort of indicia such as the letters A, B, and C shown in FIG. 1 so that the lab technician can distinguish between the various reservoirs. Prior to using the device, each reservoir will have had placed within it the desired preservative or chemical additives. The indicia serve to identify the fluid reservoirs so that the proper fluid additive/preservative combination can be used for the proper chemical analysis.

The preservatives/additives sought to be used may be placed in the container by hospital staff prior to use or alternatively the urine collecting device may be supplied by the manufacturer with various additive/preservatives installed in the various regions.

This invention has the capability of allowing the addition of a variety of chemicals to each compartment either in advance, simultaneously, or after collection to enhance, preserve, buffer, stabilize, or alter the collected composition. This is useful in increasing the precision and accuracy of subsequent analysis of said fluid. This will increase the in vitro analysis usefulness by more accurately reflecting the in vivo values we seek to evaluate. Since the collections are performed simultaneously, greater analysis of the chemical and metabolic interrelationship is possible. Preservatives can be added as a liquid, semi-permeable stick or as a crystal coating strip on the inside surface.

Figure 4:
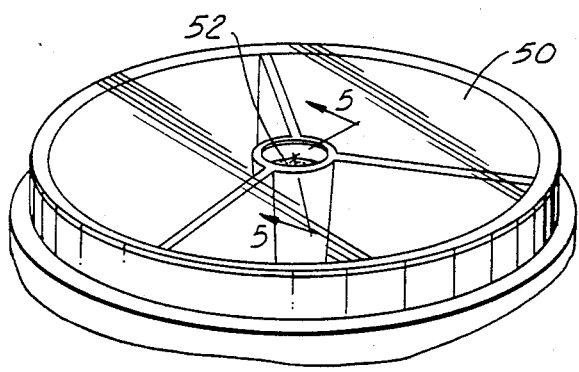
FIG. 4 is a partial perspective view of the base of an alternative embodiment of the device having a protective cover installed thereon.
Figure 5:
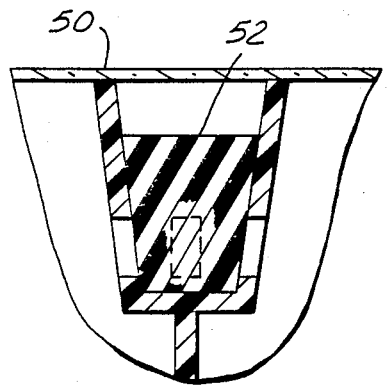
FIG. 5 is a partial cross-sectional side view of a portion of the device taken along line 5—5 in FIG. 4.
Figure 5:
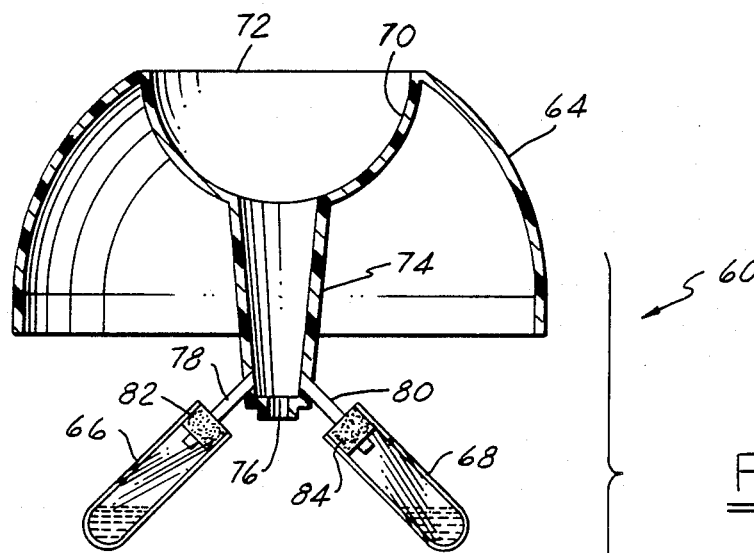

The additives may be placed on the bottom or walls of the fluid regions so that they will be dissolved upon coming in contact with urine. Preferably the additive/preservative will be painted on the side walls and partitions forming the side walls of the regions so that the amount of additive/preservative dissolved will vary as a function of urine level, i.e., a total urine output. Each time additional urine is added, the level in each of the fluid regions will increase dissolving from the walls forming the regions an effective amount of additive/preservative to maintain stability or to promote the desired chemical reaction. FIG. 4 shows an optional plastic film 50 which is sealingly affixed to the upper surface of the base 12. The film is sealingly attached to the periphery of the base as well as the upper edges of the manifold 28 and partitions 16, 18 and 20. Film 50 when employed will prevent the spilling of the urine or comingling of urine resulting from bumping or tipping the device during use or transportation. The film 50 may be removed in the test lab so that a sample may be withdraw or a pipette or syringe may be inserted through the film to withdraw a sample. Plug 52 shown in FIGS. 4 and 5 may be inserted into the manifold after a complete sample has been collected so that the three fluid regions will be independently sealed from one another assuring that there will be no cross-contamination or leakage during transportation or the subsequent introduction of contaminants. Since the urine collecting device will preferably be manufactured out of plastic so that it will be inexpensive and disposable so that there will be no need to provide means for removing the plug from the manifold once installed.

Figure 6:
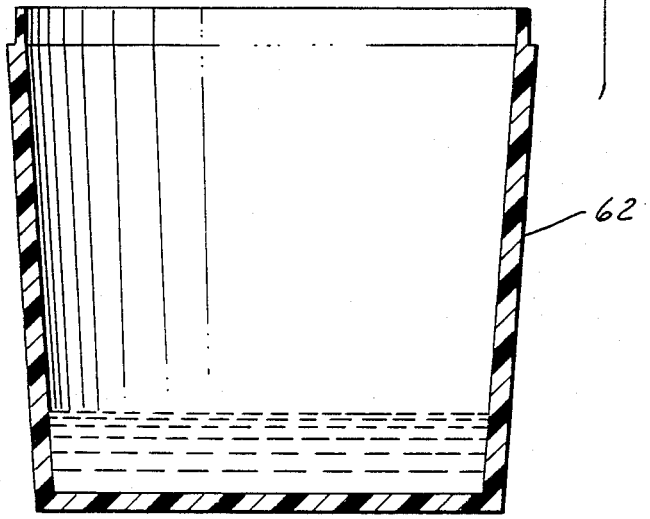
FIG. 6 is an exploded side view of another alternative embodiment of the device.

An alternative embodiment of the urine collecting device 60 is shown in cross-sectional side view in FIG. 6.

This embodiment has the added feature of collecting the timed representative samples in small modules to which additives may be added while the majority of urine is collected below through a much larger opening. A number of smaller openings at the bottom of the separator allow a very small but represesive sample to collect in the modules from each deposit.

This embodiment is similar to the first device with the added feature of collecting a small aliquot of each fluid so deposited, so as to constitute a time-weighted chemical composition identical to the deposited material, but chemically preserved, enhanced, stabilized or altered, in detachable testing modules for the purposes of preservation, reactivity, qualitative and quantitative analysis.

The urine collecting device 60 consists of a base 62, a cover 64 and two or more specimen containers 66 and 68. The cover 64 is provided with a generally funnel-shaped portion 70 having an enlarged mouth 72 and a neck portion 74. The neck terminates into the restricted orifice 76. Immediately above the orifice are a plurality of outlet ports connected to outlet tubes 78 and 80 each communicating with respective specimen containers 66 and 68. The outlet tubes shown are generally tubular in shape and project through an elastic seal 82 and 84 in the specimen containers.

When urine is poured into the mouth of the funnel, orifice 76 will provide a resistance to flow so that a small column of fluid will accumulate in neck 74 until all of the fluid has gradually passed through orifice 76. When urine is poured into the device the majority of the fluid will pass directly through orifice 76 and into the base. The remainder of the fluid will flow through outlet port 78 and 80 to be collected within specimen containers 66 and 68. This alternative embodiment collects a small aliquot from each fluid deposited in the device so that accumulated sample constitutes a time-weighted chemical composition identical to that accumulated in the base. Within each of the small specimen containers appropriate preservative and/or chemical additives may be placed in specimen container prior to use. The specimen containers can be sized so that they can be compatible with commercially available urine analyzers such as ACA ™, Dupont Discrete Clinical Analyzer. After the time collection has been completed and samples can be removed and sent directly to the laboratory with no need for further handling. Elastic seals 82 and 84 are designed such that the specimen container can be removed from the outlet port and the opening in the seal will close rendering the specimen container fluid-tight.

Preferably, both embodiments of the invention described will be formed with a disposable molded plastic material, however, it could be possible to manufacture the device using other materials such as glass. It is also preferably to fabricate the device out of a material which prevents the collected urine from being exposed to light. Light significantly stimulates bacterial growth and degradation of the collected sample. Since it is frequently desirable to measure the total quantity of urine accumulated during the test, the exterior or alternatively the interior of the base may be marked with a graduated scale to indicate the volume. If the base member is slightly transparent, at least in the region of the graduation markings, the volume can be readily determined without even opening the device.

It is also understood, of course, that while the form of the invention herein shown and described constitutes a preferred embodiment of the invention, it is not intended to illustrate all possible forms thereof. It will also be understood that the words used are words of description rather than limitation and various changes may be made without departing from the spirit and scope of the invention disclosed.

I claim:

1. A portable collection device for temporary placement on an irregular support surface to separate and store liquid said collection device comprising: a manifold having; a tapered tubular body with a large upper end and a small compact lower end, an inlet opening for receiving liquid in the upper end of the tubular body, and a plurality of outlet means adjacent to the lower end of the tubular body, for causing substantially all of the liquid poured therein to flow in equal amounts out said outlet means with minimal accumulation in said manifold, substantially unaffected by varying inclination of the tubular body.

2. The invention of claim 1 further comprising a plurality of outlet tubes each having two ends, one end communicating with an outlet means in the manifold and the other end for removably cooperating with a canister for receiving liquid.

3. The invention of claim 2 wherein said manifold is further provided with a restricted orifice in the lower end of the body sized to allow the majority of the liquid entering the manifold to exit through the orifice with the remaining portion of the liquid equally divided between said outlet means.

4. The invention of claim 3 further comprising a reservoir for receiving the liquid flowing through said orifice.

5. The invention of claim 4 further comprising a cover, said cover cooperating with said reservoir and having a funnel formed therein which directs liquid poured therein into the inlet opening of the manifold.

6. The invention of claim 1 wherein said tubular body of the manifold has a generally vertical axis and said outlet means are circumferentially spaced about and radially projecting from said axis.

7. The invention of claim 6 further comprising a reservoir having a plurality of independent liquid compartments, each of said compartments oriented to receive liquid exiting from said plurality of outlet means in the manifold.

8. The invention of claim 7 further comprising a cover, said cover cooperating with said reservoir and having a funnel formed therein to direct liquid poured into said funnel into the inlet opening of said manifold.

9. The invention of claim 8 wherein said funnel of said cover sealingly, telescopically cooperates with said inlet opening of the manifold.

10. The invention of claim 7 wherein said reservoir and said manifold are integrally formed as a single unit where said plurality of chambers in the reservoir are radially spaced adjacent to each outlet means in the manifold.

11. A portable collection device for separating and storing a plurality of liquid samples, said collecting devices comprising:
a reservoir having formed therein a plurality of independent chambers for receiving liquid; and
a manifold having a tapered tubular body with a large upper end and a small compact lower end, said upper end forming an inlet opening for receiving liquid into the body, and said lower end provided with a plurality of outlet ports, each of said outlet ports oriented to direct fluid into one of the reservoir chambers so that when liquid is poured into the manifold inlet opening, the liquid is divided into predetermined proportional amounts, substantially unaffected by varying inclination of the tubular body.

12. The invention of claim 11 wherein there are an equal number of outlet ports as there are reservoir chambers and said liquid is divided substantially equally therebetween.

13. The invention of claim 12 further comprising a cover, said cover further cooperating with said reservoir to enclose same and having a funnel shaped portion formed therein for receiving liquid, said liquid received in the funnel shaped portion is directed into the inlet opening of the manifold.

14. The invention of claim 13 wherein said funnel shaped portion sealingly, telescopically cooperates with the inlet of the manifold.

15. The invention of claim 14 wherein said manifold inwardly tapers at its lower end to cause the liquid poured therein to flow in equal amounts through said outlet ports with minimal accumulation in said manifold.

16. The invention of claim 15 wherein said funnel shaped portion is provided with a tapered outlet end sealingly, telescopically cooperating with said manifold, the outlet of said funnel shaped portion having a cross-sectional area of less than the corresponding cross-sectional area of the manifold.

17. The invention of claim 11 wherein said tubular body of the manifold has a generally vertical axis and said outlet ports are circumferentially spaced apart and radially projecting from said axis.

18. The invention of claim 11 further comprising a protective film cooperating with said reservoir and the plurality of independent chambers formed therein temporarily form a liquid tight seal between said chambers.

* * * * *